(12) United States Patent
Shellenberger

(10) Patent No.: US 12,064,115 B2
(45) Date of Patent: *Aug. 20, 2024

(54) CLIP APPLIER HAVING STABILIZING MEMBER

(71) Applicant: TELEFLEX MEDICAL INCORPORATED, Morrisville, NC (US)

(72) Inventor: Carson J. Shellenberger, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/686,909

(22) Filed: Mar. 4, 2022

(65) Prior Publication Data

US 2022/0211379 A1 Jul. 7, 2022

Related U.S. Application Data

(63) Continuation of application No. 15/927,763, filed on Mar. 21, 2018, now Pat. No. 11,266,408.

(Continued)

(51) Int. Cl.
*A61B 17/10* (2006.01)
*A61B 17/08* (2006.01)
(Continued)

(52) U.S. Cl.
CPC ............ *A61B 17/10* (2013.01); *A61B 17/083* (2013.01); *A61B 17/1285* (2013.01);
(Continued)

(58) Field of Classification Search
CPC ..... A61B 17/10; A61B 17/083; A61B 17/128; A61B 17/1285; A61B 17/068
See application file for complete search history.

(56) References Cited

U.S. PATENT DOCUMENTS

| 929,868 A | 8/1909 | Mueller |
| 1,482,290 A | 1/1924 | Peter |

(Continued)

FOREIGN PATENT DOCUMENTS

| AU | 676836 B2 | 3/1997 |
| CN | 1356092 A | 7/2002 |

(Continued)

*Primary Examiner* — Diane D Yabut
(74) *Attorney, Agent, or Firm* — BakerHostetler

(57) ABSTRACT

A clip applier may be configured to apply a surgical clip to tissue. The clip applier may include a first jaw member configured to engage a distal portion of a first leg member of the surgical clip, and a second jaw member configured to engage a distal portion of a second leg member of the surgical clip. The clip applier may further include a stabilizing member on the first jaw member. The stabilizing member may have a cavity configured to receive a proximal portion of the surgical clip and to reduce lateral movement of the surgical clip. The clip applier may not proximally abut the surgical clip when the first and second jaw members are in an open configuration. The second jaw member may also have a longitudinal channel configured to receive the stabilizing member when the first and second jaw members are in a closed configuration.

20 Claims, 9 Drawing Sheets

Related U.S. Application Data

(60) Provisional application No. 62/474,544, filed on Mar. 21, 2017.

(51) Int. Cl.
*A61B 17/128* (2006.01)
*A61B 17/00* (2006.01)
*A61B 17/122* (2006.01)
*A61B 90/00* (2016.01)

(52) U.S. Cl.
CPC . *A61B 2017/00526* (2013.01); *A61B 17/1227* (2013.01); *A61B 2090/034* (2016.02)

(56) References Cited

U.S. PATENT DOCUMENTS

| | | |
|---|---|---|
| 1,728,322 A | 9/1929 | Badrian |
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Jacobs |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,446,212 A | 5/1969 | Le Roy |
| 3,463,156 A | 8/1969 | McDermott et al. |
| 3,503,396 A | 3/1970 | Pierie et al. |
| 3,503,397 A | 3/1970 | Fogarty et al. |
| 3,503,398 A | 3/1970 | Fogarty et al. |
| 3,766,925 A | 10/1973 | Rubricius |
| 3,825,012 A | 7/1974 | Nicoll |
| 3,827,438 A | 8/1974 | Kees |
| 3,867,944 A | 2/1975 | Samuels |
| 3,874,042 A | 4/1975 | Eddleman et al. |
| 3,954,108 A | 5/1976 | Davis |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,345,600 A | 8/1982 | Rothfuss |
| 4,346,869 A | 8/1982 | MacNeill |
| 4,390,019 A | 6/1983 | Leveen et al. |
| 4,394,864 A | 7/1983 | Sandhaus |
| 4,414,721 A | 11/1983 | Hufnagel |
| 4,418,694 A | 12/1983 | Beroff et al. |
| 4,428,374 A | 1/1984 | Auburn |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di et al. |
| 4,492,232 A | 1/1985 | Green |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A | 10/1986 | Golden |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A | 10/1991 | Schmidt et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | Van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,194,938 A | 3/1993 | Imbert et al. |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | McQuilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,700,270 A | 12/1997 | Peyser |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,797,922 A | 8/1998 | Hessel et al. |
| 5,810,853 A | 9/1998 | Yoon |
| 5,833,696 A | 11/1998 | Whitfield et al. |
| 5,843,097 A | 12/1998 | Mayenberger et al. |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,997,548 A | 12/1999 | Jahanger |
| 6,010,516 A | 1/2000 | Hulka |
| 6,013,088 A | 1/2000 | Karavidas |

(56) References Cited

U.S. PATENT DOCUMENTS

| | | |
|---|---|---|
| 6,015,417 A | 1/2000 | Reynolds, Jr. |
| 6,050,996 A | 4/2000 | Schmaltz et al. |
| 6,131,576 A | 10/2000 | Davis |
| 6,158,583 A | 12/2000 | Forster |
| 6,210,419 B1 | 4/2001 | Mayenberger et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,253 B1 | 8/2001 | Forster |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,558,408 B1 | 5/2003 | Fogarty et al. |
| 6,599,298 B1 | 7/2003 | Forster et al. |
| 6,695,854 B1 | 2/2004 | Kayan et al. |
| 6,699,258 B1 | 3/2004 | Sadler et al. |
| 6,719,766 B1 | 4/2004 | Buelna et al. |
| 6,773,438 B1 | 8/2004 | Knodel et al. |
| 6,780,195 B2 | 8/2004 | Porat |
| 6,814,742 B2 | 11/2004 | Kimura et al. |
| 6,824,547 B2 | 11/2004 | Wilson et al. |
| 6,837,895 B2 | 1/2005 | Mayenberger |
| 6,843,253 B2 | 1/2005 | Parkes |
| 6,863,675 B2 | 3/2005 | Wilson, Jr. |
| 6,880,699 B2 | 4/2005 | Gallagher |
| 6,926,712 B2 | 8/2005 | Phan |
| 6,932,816 B2 | 8/2005 | Phan |
| 6,989,017 B2 | 1/2006 | Howell et al. |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,131,977 B2 | 11/2006 | Fowler |
| 7,179,265 B2 | 2/2007 | Manetakis et al. |
| 7,211,091 B2 | 5/2007 | Fowler et al. |
| 7,211,092 B2 | 5/2007 | Hughett |
| 7,261,724 B2 | 8/2007 | Molitor et al. |
| 7,316,696 B2 | 1/2008 | Wilson et al. |
| 7,326,223 B2 | 2/2008 | Wilson, Jr. |
| 7,329,266 B2 | 2/2008 | Royse et al. |
| 7,357,805 B2 | 4/2008 | Masuda et al. |
| 7,402,164 B2 | 7/2008 | Watson et al. |
| 7,572,266 B2 | 8/2009 | Young et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,648,514 B1 | 1/2010 | Nakao |
| 7,727,231 B2 | 6/2010 | Swanson |
| 7,753,908 B2 | 7/2010 | Swanson |
| 7,785,324 B2 | 8/2010 | Eberl |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,142,451 B2 | 3/2012 | Boulnois et al. |
| 8,262,639 B2 | 9/2012 | Mathias |
| 8,403,138 B2 | 3/2013 | Weisshaupt et al. |
| 8,425,412 B2 | 4/2013 | Rucker |
| 8,465,507 B2 | 6/2013 | Cosgrove et al. |
| 8,512,357 B2 | 8/2013 | Mola |
| 8,585,718 B2 | 11/2013 | Disch et al. |
| 8,764,774 B2 | 7/2014 | Sigmon, Jr. |
| 8,839,954 B2 | 9/2014 | Disch |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,737,309 B1 | 8/2017 | Ad |
| 9,775,635 B2 | 10/2017 | Takei |
| 9,855,053 B2 | 1/2018 | Bagaoisan et al. |
| 9,901,352 B2 | 2/2018 | Fago et al. |
| 9,955,977 B2 | 5/2018 | Martinez et al. |
| 10,064,623 B2 | 9/2018 | Soutorine et al. |
| 10,136,898 B2 | 11/2018 | Schmidt et al. |
| 10,285,712 B2 | 5/2019 | Cosgrove et al. |
| 10,292,712 B2 | 5/2019 | Shankarsetty |
| 10,307,166 B2 | 6/2019 | Willett et al. |
| 10,383,637 B2 | 8/2019 | Castro |
| 10,548,609 B2 | 2/2020 | Ramsey et al. |
| 10,758,243 B2 | 9/2020 | Salas |
| 10,925,616 B2 | 2/2021 | Shellenberger et al. |
| 11,160,550 B2 | 11/2021 | Harris |
| 11,160,559 B2 | 11/2021 | Shellenberger |
| 11,266,408 B2 | 3/2022 | Shellenberger |
| 11,576,680 B2 | 2/2023 | Ramsey |
| 11,607,227 B2 | 3/2023 | Shellenberger |
| 2002/0046961 A1 | 4/2002 | Levinson et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0014060 A1 | 1/2003 | Wilson et al. |
| 2003/0074009 A1 | 4/2003 | Ramsey et al. |
| 2003/0158548 A1 | 8/2003 | Phan et al. |
| 2004/0010272 A1 | 1/2004 | Manetakis et al. |
| 2004/0040875 A1 | 3/2004 | Gallagher |
| 2004/0044352 A1 | 3/2004 | Fowler |
| 2004/0059359 A1 | 3/2004 | Wilson |
| 2004/0097970 A1 | 5/2004 | Hughett |
| 2004/0172043 A1 | 9/2004 | Watson et al. |
| 2005/0090838 A1 | 4/2005 | Sixto et al. |
| 2005/0149063 A1 | 7/2005 | Young et al. |
| 2005/0149068 A1 | 7/2005 | Williams et al. |
| 2005/0149069 A1 | 7/2005 | Bertolero et al. |
| 2005/0165421 A1 | 7/2005 | Wilson et al. |
| 2005/0165422 A1 | 7/2005 | Wilson |
| 2005/0165423 A1 | 7/2005 | Gallagher et al. |
| 2005/0165429 A1 | 7/2005 | Douglas et al. |
| 2005/0171560 A1 | 8/2005 | Hughett |
| 2005/0234478 A1 | 10/2005 | Wixey et al. |
| 2005/0240219 A1 | 10/2005 | Kahle et al. |
| 2005/0277959 A1 | 12/2005 | Cosgrove et al. |
| 2006/0217749 A1 | 9/2006 | Wilson et al. |
| 2007/0016228 A1 | 1/2007 | Salas |
| 2007/0049947 A1 | 3/2007 | Menn et al. |
| 2007/0083218 A1 | 4/2007 | A. Morris |
| 2007/0118161 A1 | 5/2007 | Kennedy et al. |
| 2007/0149989 A1 | 6/2007 | Santilli et al. |
| 2007/0276417 A1 | 11/2007 | Mendes et al. |
| 2007/0282355 A1 | 12/2007 | Brown et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0112233 A1 | 4/2009 | Xiao |
| 2009/0171380 A1 | 7/2009 | Whiting |
| 2009/0240266 A1 | 9/2009 | Dennis |
| 2010/0057107 A1 | 3/2010 | Sorrentino et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274262 A1 | 10/2010 | Schulz et al. |
| 2010/0274264 A1 | 10/2010 | Schulz et al. |
| 2010/0274268 A1 | 10/2010 | Singh et al. |
| 2011/0022079 A1 | 1/2011 | Miles et al. |
| 2011/0087244 A1 | 4/2011 | Weisshaupt et al. |
| 2011/0144665 A1 | 6/2011 | Malkowski |
| 2011/0245848 A1 | 10/2011 | Rosenberg et al. |
| 2011/0295291 A1 | 12/2011 | Trivisani |
| 2012/0074200 A1 | 3/2012 | Schmid et al. |

(56) References Cited

U.S. PATENT DOCUMENTS

| | | |
|---|---|---|
| 2012/0083803 A1 | 4/2012 | Patel et al. |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0253535 A1 | 9/2013 | Pribanic et al. |
| 2013/0261642 A1 | 10/2013 | Willett et al. |
| 2014/0018830 A1 | 1/2014 | Shelton, IV |
| 2014/0058411 A1 | 2/2014 | Soutorine et al. |
| 2014/0207156 A1 | 7/2014 | Malkowski |
| 2014/0243862 A1 | 8/2014 | Bagaoisan et al. |
| 2014/0309677 A1 | 10/2014 | Baldwin |
| 2015/0066057 A1 | 3/2015 | Malkowski et al. |
| 2015/0136835 A1 | 5/2015 | Shelton, IV et al. |
| 2015/0190137 A1 | 7/2015 | Salas |
| 2015/0320426 A1 | 11/2015 | Cosgrove et al. |
| 2016/0151073 A1 | 6/2016 | Castro et al. |
| 2016/0174981 A1 | 6/2016 | Fago et al. |
| 2016/0213377 A1 | 7/2016 | Shankarsetty |
| 2016/0256157 A1 | 9/2016 | Rockrohr et al. |
| 2016/0270790 A1 | 9/2016 | Jankowski |
| 2016/0354089 A1 | 12/2016 | Whiting |
| 2017/0014135 A1 | 1/2017 | Martin et al. |
| 2017/0238935 A1 | 8/2017 | Shi |
| 2018/0036008 A1 | 2/2018 | Ramsey et al. |
| 2018/0168659 A1 | 6/2018 | Bagaoisan et al. |
| 2018/0271527 A1 | 9/2018 | Shellenberger |
| 2018/0271532 A1 | 9/2018 | Shellenberger |
| 2018/0271534 A1 | 9/2018 | Shellenberger |
| 2018/0271535 A1 | 9/2018 | Shellenberger et al. |
| 2018/0271536 A1 | 9/2018 | Shellenberger et al. |
| 2021/0128159 A1 | 5/2021 | Taylor et al. |
| 2022/0047271 A1 | 2/2022 | Shellenberger |

FOREIGN PATENT DOCUMENTS

| | | |
|---|---|---|
| CN | 1846638 A | 10/2006 |
| CN | 101543418 A | 9/2009 |
| CN | 103181809 A | 7/2013 |
| CN | 103442658 A | 12/2013 |
| CN | 103930054 A | 7/2014 |
| CN | 104367363 A | 2/2015 |
| CN | 104414701 A | 3/2015 |
| CN | 105054989 A | 11/2015 |
| CN | 105078536 A | 11/2015 |
| CN | 105816217 A | 8/2016 |
| CN | 106037947 A | 10/2016 |
| CN | 106264646 A | 1/2017 |
| CN | 110740696 A | 1/2020 |
| EP | 0086640 A2 | 8/1983 |
| EP | 0201344 A2 | 11/1986 |
| EP | 0314064 A2 | 5/1989 |
| EP | 0576835 A2 | 1/1994 |
| EP | 1233705 A2 | 8/2002 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| IN | 104039248 A | 9/2014 |
| JP | 56-151034 A | 11/1981 |
| JP | 61-007818 B2 | 3/1986 |
| JP | 61-259652 A | 11/1986 |
| JP | 03-178648 A | 8/1991 |
| JP | 05-200039 A | 8/1993 |
| JP | 2002-345828 A | 12/2002 |
| JP | 2004-522468 A | 7/2004 |
| JP | 2004-535236 A | 11/2004 |
| JP | 4263594 B2 | 5/2009 |
| JP | 2011-036675 A | 2/2011 |
| JP | 2011-517423 A | 6/2011 |
| JP | 2014-531250 A | 11/2014 |
| JP | 2015-043977 A | 3/2015 |
| WO | 97/38634 A1 | 10/1997 |
| WO | 01/35837 A1 | 5/2001 |
| WO | 01/37742 A2 | 5/2001 |
| WO | 2004/043225 A2 | 5/2004 |
| WO | 2005/107613 A1 | 11/2005 |
| WO | 2006/102578 A1 | 9/2006 |
| WO | 2012/075532 A1 | 6/2012 |
| WO | 2013/040467 A2 | 3/2013 |
| WO | 2015/099067 A1 | 7/2015 |
| WO | 2016/094647 A1 | 6/2016 |
| WO | 2018/027032 A1 | 2/2018 |
| WO | 2018/175626 A1 | 9/2018 |
| WO | 2020/018784 A1 | 1/2020 |

CLIP APPLIER HAVING STABILIZING MEMBER

PRIORITY

The present is a continuation of U.S. application Ser. No. 15/927,763, filed Mar. 21, 2018, which claims the benefit of U.S. Provisional Application No. 62/474,544 filed Mar. 21, 2017, the disclosures of which are incorporated by reference in their entirety.

TECHNICAL FIELD

The present disclosure relates generally to clip appliers, and more particularly, to clip appliers having a stabilizing member.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventor recognizes that there is a need to improve one or more features of the clip appliers and/or surgical clips, such as stability of the surgical clip in a clip applier. Surgical clips are often applied by clip appliers with a pair of opposing jaw members. Currently available clip appliers often secure the clip with two points of contact between the opposing jaw members and the leg members of the surgical clip. The two points of contact do not provide sufficient stability for the surgical clip, which can unfavorably move relative to the clip applier during a surgical procedure, or even fall out of the jaw members. The disclosed methods and systems are directed to mitigating or overcoming one or more of the problems set forth above and/or other problems in the prior art.

A first aspect of the present disclosure is directed to a clip applier configured to apply a surgical clip to tissue. The clip applier may include a first jaw member configured to engage a distal portion of a first leg member of the surgical clip, and a second jaw member configured to engage a distal portion of a second leg member of the surgical clip. The clip applier may further include a stabilizing member on the first jaw member. The stabilizing member may have a cavity configured to receive a proximal portion of the surgical clip and to reduce lateral movement of the surgical clip.

In some embodiments, the clip applier does not proximally abut the surgical clip when the first and second jaw members are in an open configuration. In some embodiments, the second jaw member may include a longitudinal channel configured to receive the stabilizing member when the first and second jaw members are in a closed configuration. In some embodiments, the stabilizing member may include first and second longitudinal walls configured to receive the proximal portion of the surgical clip when the first and second jaw members are in an open configuration. In some embodiments, the first and second longitudinal walls have substantially flat inner side surfaces. In some embodiments, a proximal end of the cavity is closed. In some embodiments, a proximal end of the cavity is open. In some embodiments, the stabilizing member is configured to slide over the proximal portion when the clip applier closes. In some embodiments, the clip applier may include at least one first recess on the distal portion of the first jaw member, the at least one first recess being configured to receive a boss member on the distal portion of the first leg member; and at least one second recess on the distal portion of the second jaw member, the at least one first recess being configured to receive a boss member on the distal portion of the second leg member. In some embodiments, the stabilizing member is integrated into an inner surface of the first jaw member. In some embodiments, the stabilizing member may be removably secured to the first jaw member. In some embodiments, the first jaw member may include a longitudinal channel configured to receive a portion of the first leg member.

A second aspect of the present disclosure is directed to a method of loading a clip applier with a surgical clip, where the surgical clip has first and second leg members. The method may include engaging a distal portion of the first leg member with a first jaw member of the clip applier, engaging a distal portion of the second leg member with a second jaw member of the clip applier, and receiving a proximal portion of the surgical clip in a cavity of a stabilizing member to reduce lateral movement of the surgical clip. In some embodiments, receiving the proximal portion of the surgical clip may include receiving the proximal portion between first and second longitudinal walls of the stabilizing member. In some embodiments, receiving a proximal portion of the surgical clip providing a space proximal of the proximal portion when the first and second jaw members are in an open configuration to allow at least one of the first and second leg members to lengthen during closure of the surgical clip. In some embodiments, the method may further include pivoting the first and second jaw members into a closed configuration, sliding the stabilizing member over the proximal portion, and receiving the stabilizing member in a longitudinal channel of the second jaw member in the closed configuration. In some embodiments, engaging the distal portion of the first leg member may include receiving a boss member into at least one recess on the distal portion of the first jaw member, and engaging the distal portion of the second leg member includes receiving a boss member into at least one recess on the distal portion of the second jaw member. In some embodiments, the method may further include receiving a portion of the first leg member in a longitudinal channel of the first leg member. In some embodiments, the method may further include removing the stabilizing member from the first jaw member.

A third aspect of the present disclosure is directed to a surgical clip assembly having a surgical clip and a clip applier. The surgical clip may include a first leg member having a first boss member at a distal portion and a second leg member having a second boss member at a distal portion. The clip applier may include a first jaw member having a recess on a distal portion receiving the first boss member, a second jaw member having a recess on a distal portion receiving the second boss member and a longitudinal channel, and a stabilizing member on the first jaw member. The stabilizing member may have first and second longitudinal walls defining a cavity that receives a proximal portion of the surgical clip to reduce lateral movement of the surgical clip. The clip applier does not proximately abut the proximal portion of the surgical clip when the first and second jaw members are in an open configuration, and the longitudinal channel may receive the stabilizing member when the first and second jaw members are in a closed configuration.

BRIEF DESCRIPTION OF THE DRAWINGS

In order that the disclosure may be readily understood, aspects of this disclosure are illustrated by way of examples in the accompanying drawings.

The same or similar reference numbers may be used in the drawings and the following detailed description to refer to the same or similar parts.

DETAILED DESCRIPTION

Figure 1A:
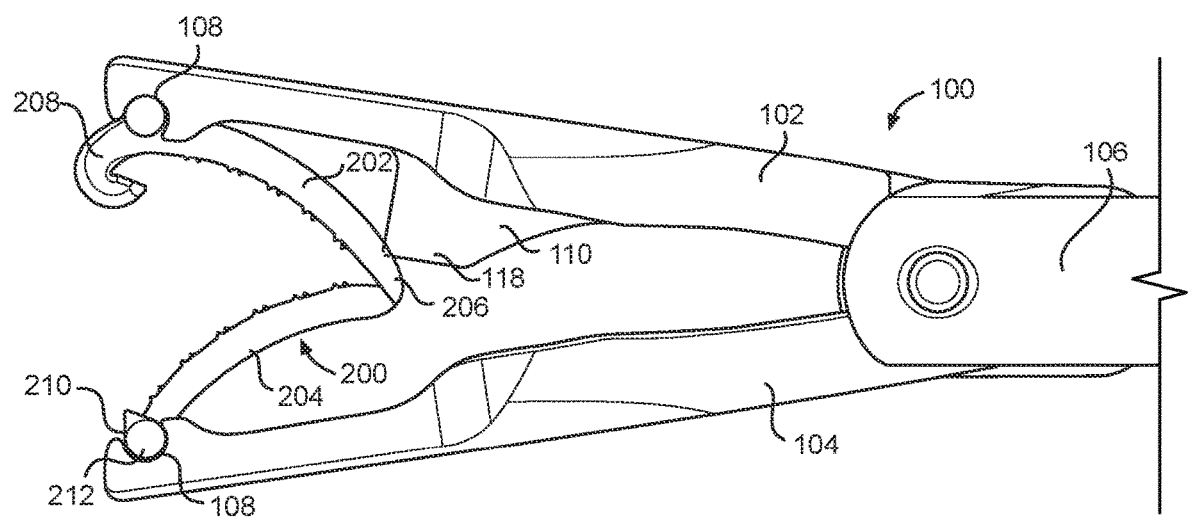
FIG. 1A illustrates a side view of a first exemplary embodiment of a clip applier having an exemplary stabilizing member and loaded with an exemplary surgical clip of the present disclosure.

The invention will now be described with reference to the figures, in which like reference numerals may refer to like parts throughout. In accordance with conventional practice, as used herein, and unless otherwise indicated herein, the term "proximal portion" refers to the specified portion of a device or its component that is generally closer to the medical personnel handling or manipulating the device as it is intended to be used, and the term "distal portion" shall refer to the specified portion of a device or its component that is opposite the proximal portion.

The present invention is generally directed to clip appliers configured to increase stability of surgical clips during a medical procedure. The clip appliers may include a clip applier having first and second jaw members with a stabilizing member disposed on at least one of the jaw members. The stabilizing member and the pair of jaw members may provide at least three points of contact with the surgical clip to reduce motion of the surgical clip relative to the clip applier during the procedure. The stabilizing member may include first and second longitudinal walls that receive a proximal portion of the surgical clip therebetween and reduce lateral movement of the surgical clip. A corner of the first and second longitudinal walls may overlap the proximal portion (e.g., at or near a hinge member) to reduce lateral movement. However, the stabilizing member may not proximally abut the proximal portion when the surgical clip is received between the jaw members. In other words, the stabilizing member may engage upper, lower, and/or sides surfaces of the proximal portion of the surgical clip when in the open configuration, but the clip applier and stabilizing member provides space proximal of the surgical clip to allow pivoting and/or lengthening of leg members of the surgical clip during closure. In some embodiments, the stabilizing member may be disposed on the first jaw member and be received in a longitudinal channel of the second jaw member in a closed configuration. The longitudinal channel of the second jaw may therefore have a narrow distal portion and a wider proximal portion that receives the stabilizing member in the closed configuration. This may allow the stabilizing member to have sufficient length to stabilize the surgical clip when the clip applier is in an open configuration, but not interfere with closure of the clip applier. The stabilizing member may include first and second longitudinal walls defining a longitudinal space or cavity therebetween. The stabilizing member may be integrated or removably secured to at least one of the first and second jaw members. Integrating the stabilizing member into at least one of the first and second jaw members may be especially preferable in some application because it facilitates the manufacturing process. However, in some applications, it may be preferable to have the stabilizing member removably secured to a jaw member, for example, to accommodate for surgical clips of different sizes and be easily replaceable when the stabilizing member is damaged.

Figure 1B:
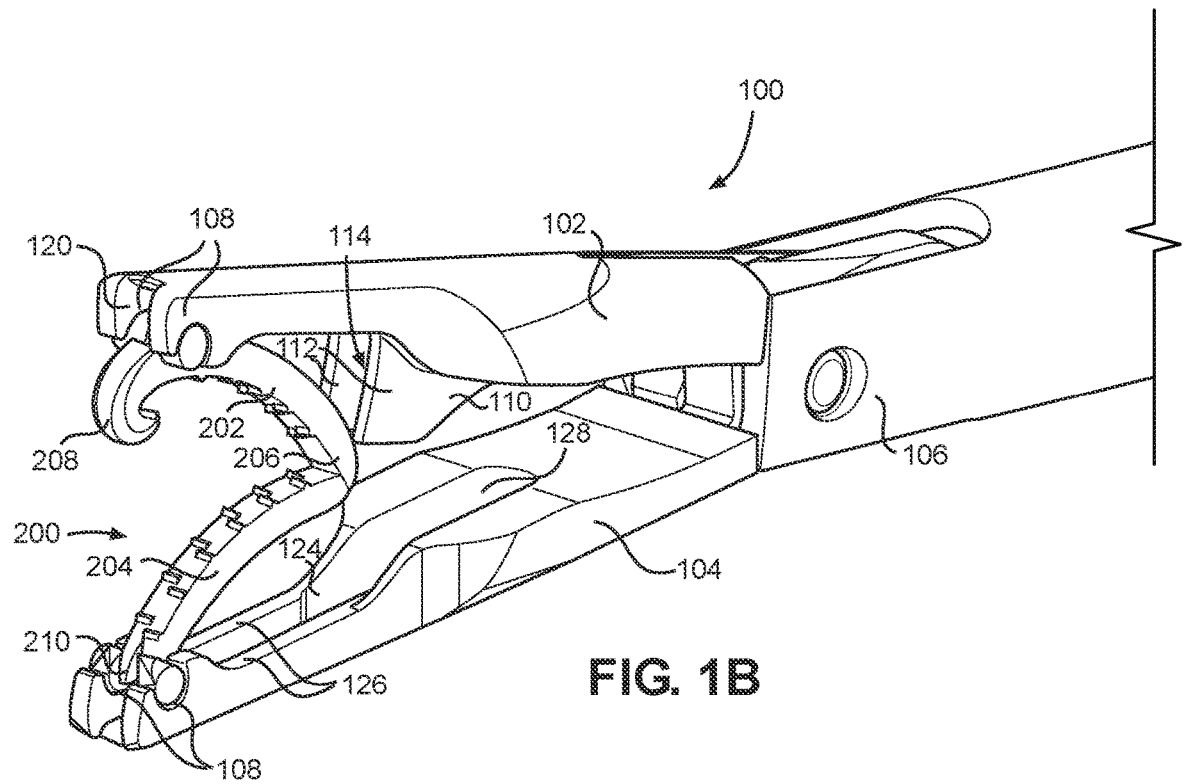
FIG. 1B illustrates a first perspective view of the first exemplary embodiment of FIG. 1A.
Figure 2:
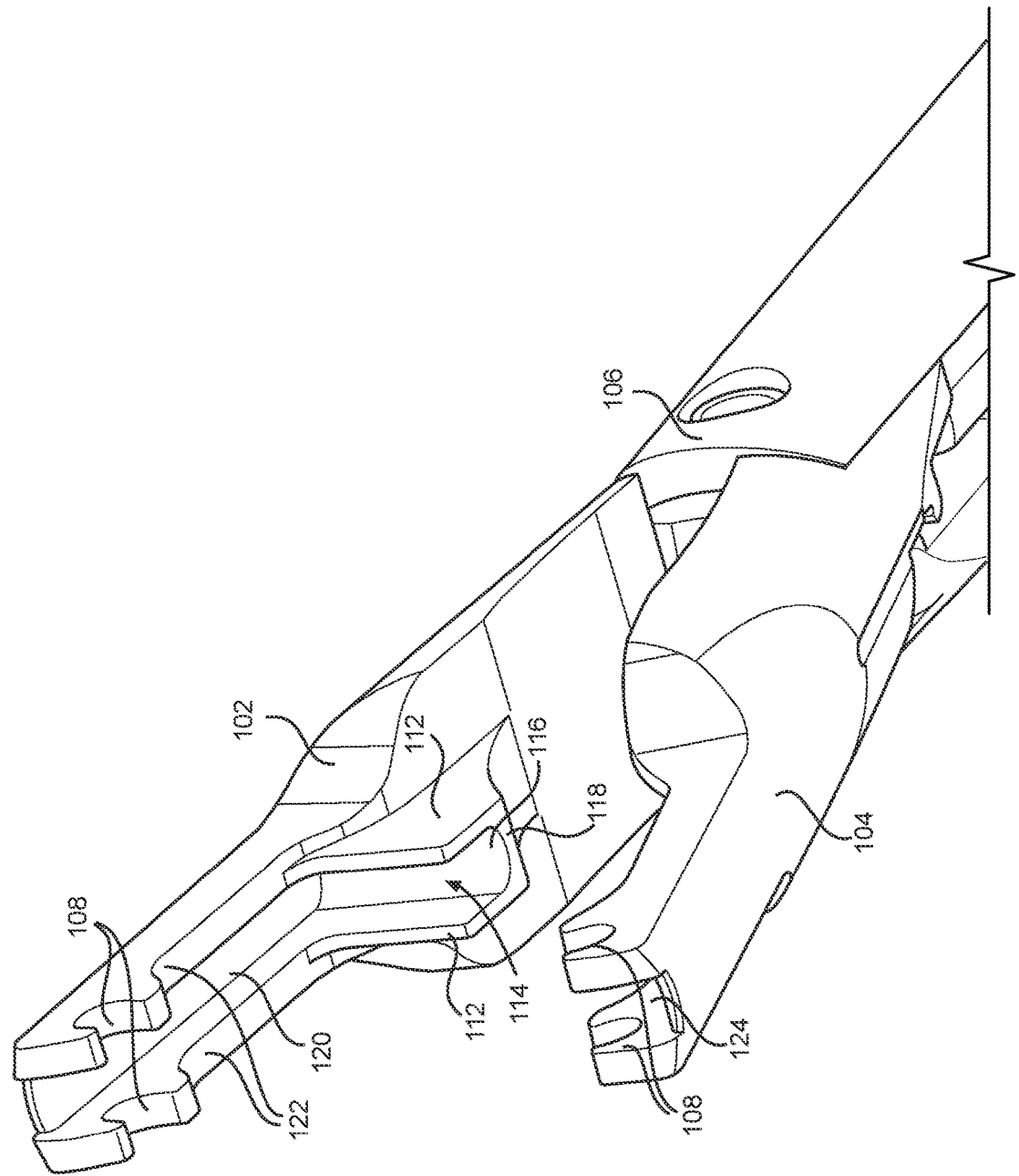
FIG. 2 illustrates a second perspective view of the exemplary clip applier of the first exemplary embodiment of FIGS. 1A-B.
Figure 3A:
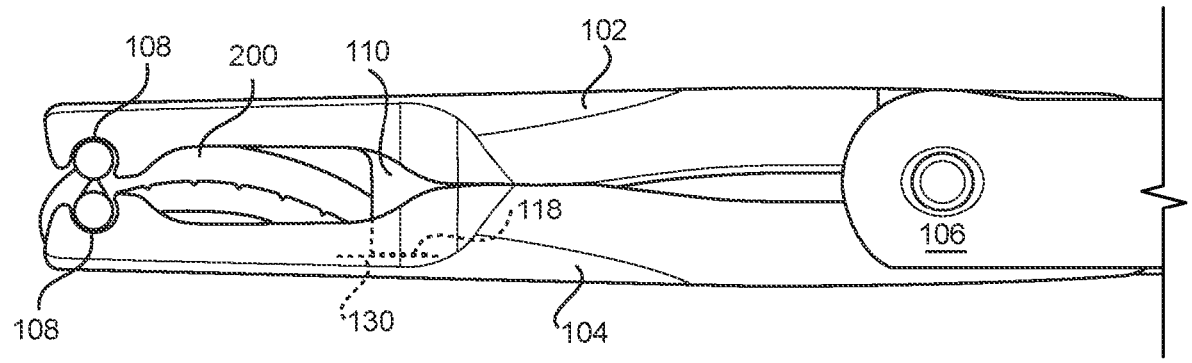
FIG. 3A illustrates a side view of the first exemplary embodiment of FIGS. 1A-2 in a closed configuration.
Figure 3B:
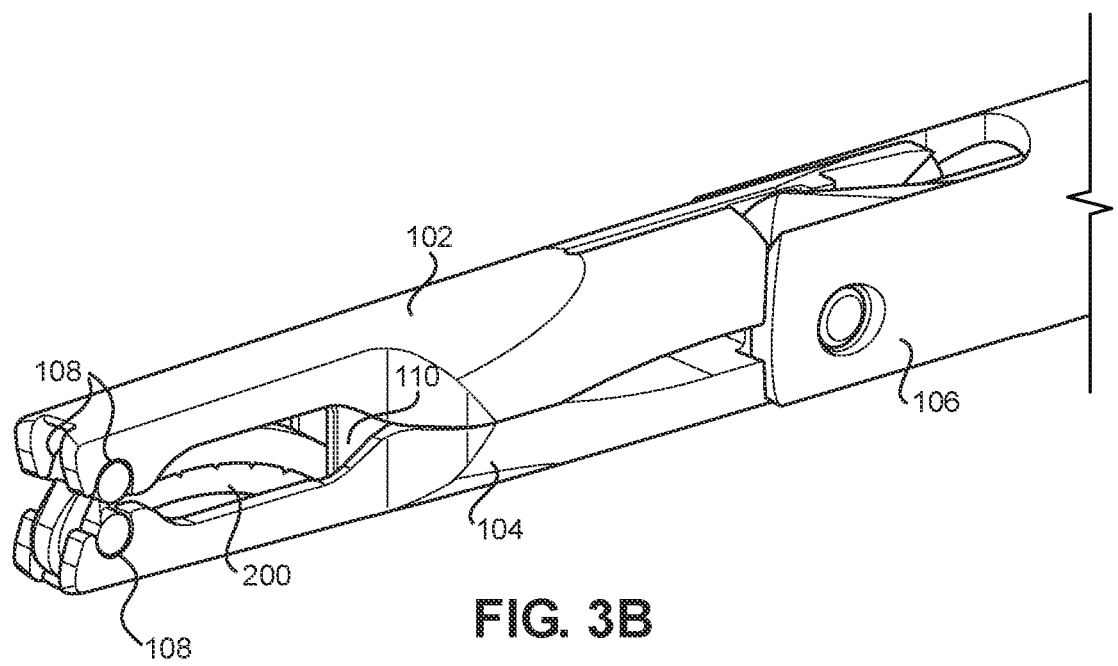
FIG. 3B illustrates a perspective view of the first exemplary embodiment of FIGS. 1A-3A in the closed configuration.

FIGS. 1A-B illustrate a clip applier 100 loaded with a surgical clip 200 in an open configuration, FIG. 2 illustrates the clip applier 100 without the surgical clip 200, and FIGS. 3A-B illustrate the clip applier 100 loaded with the surgical clip 200 in a closed configuration. As illustrated, the clip applier 100 may have a first jaw member 102 and a second jaw member 104 pivotably coupled at a hinge member 106. The first and second jaw members 102, 104 may be configured to compress the surgical clip 200 onto tissue, for example, to ligate a blood vessel.

The surgical clip 200 may have a first leg member 202 and a second leg member 204 pivotably joined at a hinge member 206. The first leg member 202 may have a generally concave inner surface, a generally convex outer surface, and a hook member 208 on a distal end. The second leg member 204 may have a generally convex inner surface, a generally concave outer surface, and a tip member 210 on a distal end. The hook member 208 may engage and deflect around the tip member 210, while one or both of the first and second leg members 202, 204 pivot, straighten, and/or lengthen. The tip member 210 may then be received in the hook member 208 to secure the surgical clip 200 in a latched configuration. Each of the first and second leg members 202, 204, may have one or more boss members 212 on a distal portion. An exemplary embodiment of the surgical clip 200 is further described in U.S. Pat. No. 4,834,096, the disclosure of which is expressly incorporated herein in its entirety. However, it is contemplated that the clip applier 100 may be configured to apply any number of embodiments of the surgical clip 200.

As further illustrated, the first and second jaw members 102, 104 may include at least one recess 108 at a distal portion and a stabilizing member 110 proximal of the at least one recess 108. The at least one recess 108 may extend transversely through the first and second jaw members 102, 104 and be configured to receive a boss member 212 on the first and second leg members 202, 204 of the surgical clip 200 in an interference or snap-fit. A first longitudinal channel 120 may extend through an inner portion of the first jaw member 102, separating the first jaw member 102 into a pair of first extensions 122. A second longitudinal channel 124 may extend through an inner portion of the second jaw member 104, separating the second jaw member 104 into a pair of second extensions 126. Each of the extensions 122, 126 may have a recess 108 configured to receive opposing boss members 212, and each of the first and second longitudinal channels 120, 124 may be configured to receive a portion of the surgical clip 200. The second longitudinal channel 124 may include a wider proximal portion 128 (as illustrated in FIG. 1B) configured to receive the stabilizing member 110 when the first and second jaw members 102, 104 are in a closed configuration (as illustrated in FIGS. 3A-B).

The stabilizing member 110 may be configured to align the surgical clip 200 by reducing lateral movement of a proximal portion. The stabilizing member 110 may be integral to the first jaw member 102 and extend inwardly toward the second jaw member 104. The stabilizing member 110 may have first and second longitudinal walls 112 having substantially flat inner and/or outer side surfaces that do not hinder closure of the clip applier 100 and/or the surgical clip 200. The longitudinal walls 112 may define a cavity 114 therebetween, and the longitudinal walls 112 may be joined at a proximal portion 116 of the stabilizing member 110 to close the cavity 114 at the proximal end. The stabilizing member 110 may not proximally abut the proximal portion of the surgical clip 200 when the first and second jaw members 102, 104 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 110 may have an inner portion 118 (e.g., the corners of the longitudinal walls 112) that overlaps the surgical clip 200 when the first and second jaw members 102, 104 are in an open configuration. Therefore, in the open configuration, the stabilizing member 110 may receive the surgical clip in the cavity 114, and the first and second longitudinal walls 112 may overlap the proximal portion of the surgical clip 200. As the first and second jaw members 102, 104 close, the stabilizing member 110 may slide over the proximal portion of the surgical clip 200, and the second longitudinal channel 124 may receive the stabilizing member 110 while the surgical clip 200 is received in the cavity 114. The inner portion 118 may also have a substantially flat inner surface that abuts a substantially flat inner wall 130 of the second longitudinal channel 124 in the closed configuration to provide a stop (as illustrated in FIG. 3A). The stabilizing member 110 may also have a distal surface extending substantially perpendicular from the first jaw member 102, and a proximal surface extending distally at an acute angle from the first jaw member 102.

Figure 4:
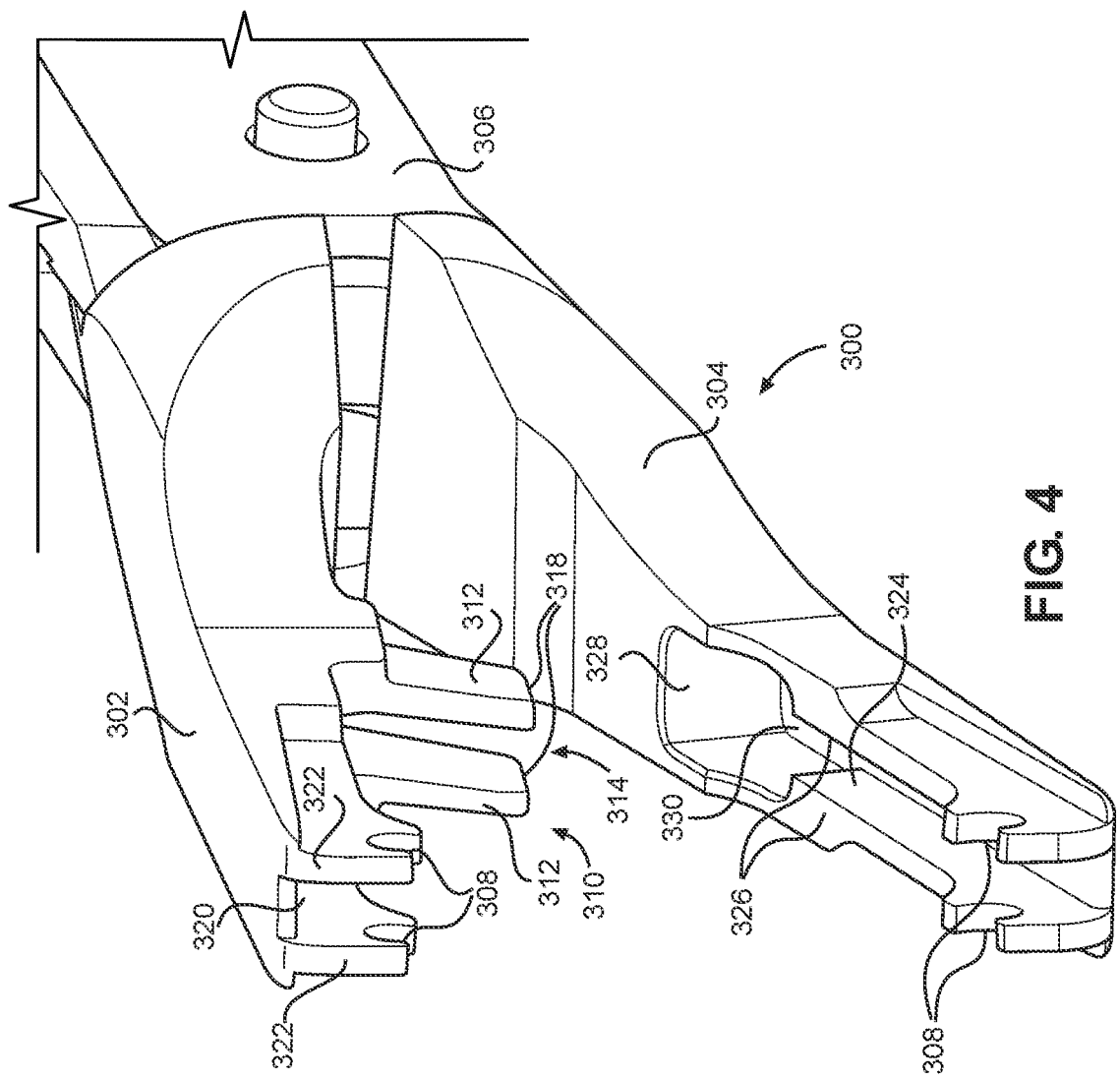
FIG. 4 illustrates a perspective view of a second exemplary embodiment of a clip applier having an exemplary stabilizing member of the present disclosure.

FIG. 4 illustrates a clip applier 300 in an open configuration. As illustrated, the clip applier 300 may have a first jaw member 302 and a second jaw member 304 pivotably coupled at a hinge member 306. The first and second jaw members 302, 304 may be configured to be loaded with the surgical clip 200 and compress the surgical clip 200 onto tissue, as similarly discussed above.

As further illustrated, the first and second jaw members 302, 304 may include at least one recess 308 at a distal portion and a stabilizing member 310 proximal of the at least one recess 308. The at least one recess 308 may extend transversely through the first and second jaw members 302, 304 and be configured to receive a boss member 212 on the first and second leg members 202, 204 of the surgical clip 200 in an interference or snap-fit. A first longitudinal channel 320 may extend through an inner portion of the first jaw member 302, separating the first jaw member 302 into a pair of first extensions 322. A second longitudinal channel 324 may extend through an inner portion of the second jaw member 304, separating the second jaw member 304 into a pair of second extensions 326. Each of the extensions 322, 326 may have a recess 308 configured to receive opposing boss members 212, and each of the first and second longitudinal channels 320, 324 may be configured to receive a portion of the surgical clip 200. The second longitudinal channel 324 may include a wider proximal portion 328 configured to receive the stabilizing member 310 when the first and second jaw members 302, 304 are in a closed configuration (as similarly illustrated in FIGS. 3A-B).

The stabilizing member 310 may be configured to align the surgical clip 200 by reducing lateral movement of a proximal portion. The stabilizing member 310 may be integral to the first jaw member 302 and extend inwardly toward the second jaw member 304. The stabilizing member 310 may have first and second longitudinal walls 312 having substantially inner and/or outer side surfaces that do not hinder closure of the clip applier 100 and/or the surgical clip 200. The longitudinal walls 312 may define a cavity 314 therebetween, and the longitudinal walls 312 may be spaced at a proximal portion to provide an open proximal end of the cavity 314. The stabilizing member 310 may not proximally abut the proximal portion of the surgical clip 200 when the first and second jaw members 302, 304 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 310 may have an inner portion 318 (e.g., the corners of the longitudinal walls 312) that overlaps the surgical clip 200 when the first and second jaw members 302, 304 are in an open configuration. Therefore, in the open configuration, the stabilizing member 310 may receive the surgical clip in the cavity 314, and the first and second longitudinal walls 312 may overlap the proximal portion of the surgical clip 200. As the first and second jaw members 302, 304 close, the stabilizing member 310 may slide over the proximal portion of the surgical clip 200, and the second longitudinal channel 324 may receive the stabilizing member 310 while the surgical clip 200 is received in the cavity 314. The inner portion 318 may also have a substantially flat inner surface that abuts a substantially flat inner wall 330 of the second longitudinal channel 324 in the closed configuration to provide a stop. The stabilizing member 310 may also have a distal surface extending distally at an acute angle from the first jaw member 302, and a proximal surface extending distally at an acute angle from the first jaw member 302.

Figure 5A:
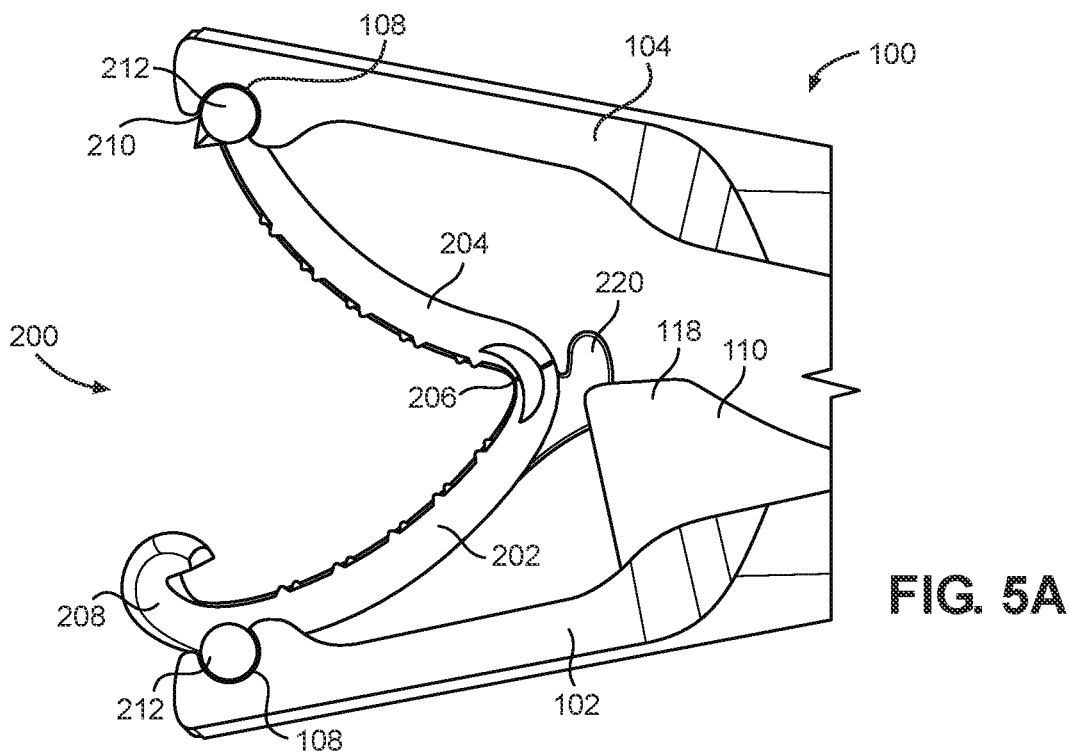
FIGS. 5A-B illustrate side views of an exemplary embodiment of an exemplary surgical clip loaded into an exemplary clip applier of the present disclosure.
Figure 5B:
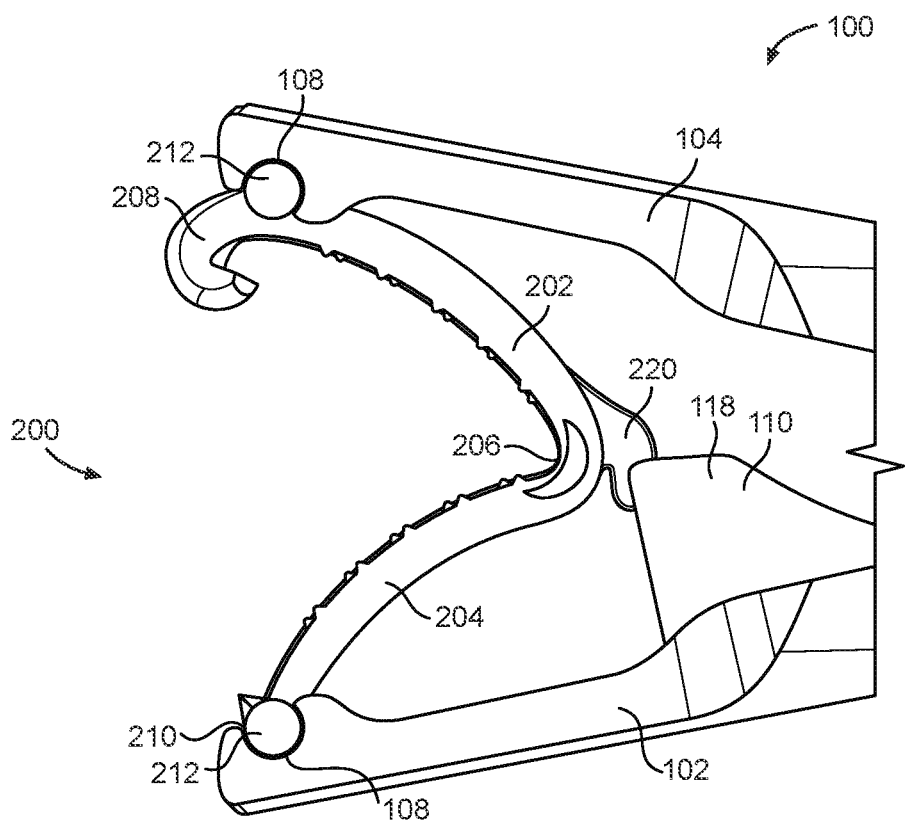

FIGS. 5A-5B illustrate a second embodiment of the surgical clip 200 loaded into the clip applier 100. As illustrated, the surgical clip 200 may include a tail or extension member 220 extending from the proximal portion of the surgical clip 200 configured to be received in the stabilizing member 110. The extension member 220 may extend proximally from a proximal portion (e.g., the hinge portion 206) and have a hook portion that curves vertically. The extension member 220 may have a width less than a width of the hinge portions 206 and/or the leg members 202, 204. The extension member 220 may facilitate loading of the surgical clip 200 into the first and second jaw members 102, 104 and into the cavity 114, when the surgical clip 200 is in either orientation, as illustrated in FIGS. 5A-B. Although FIGS. 5A-B illustrate the second embodiment of the surgical clip 200 being loaded into the clip applier 100, the second embodiment of the surgical clip 200 may be loaded into any number of other clip appliers, including the other embodiments of the present disclosure.

Figure 6:
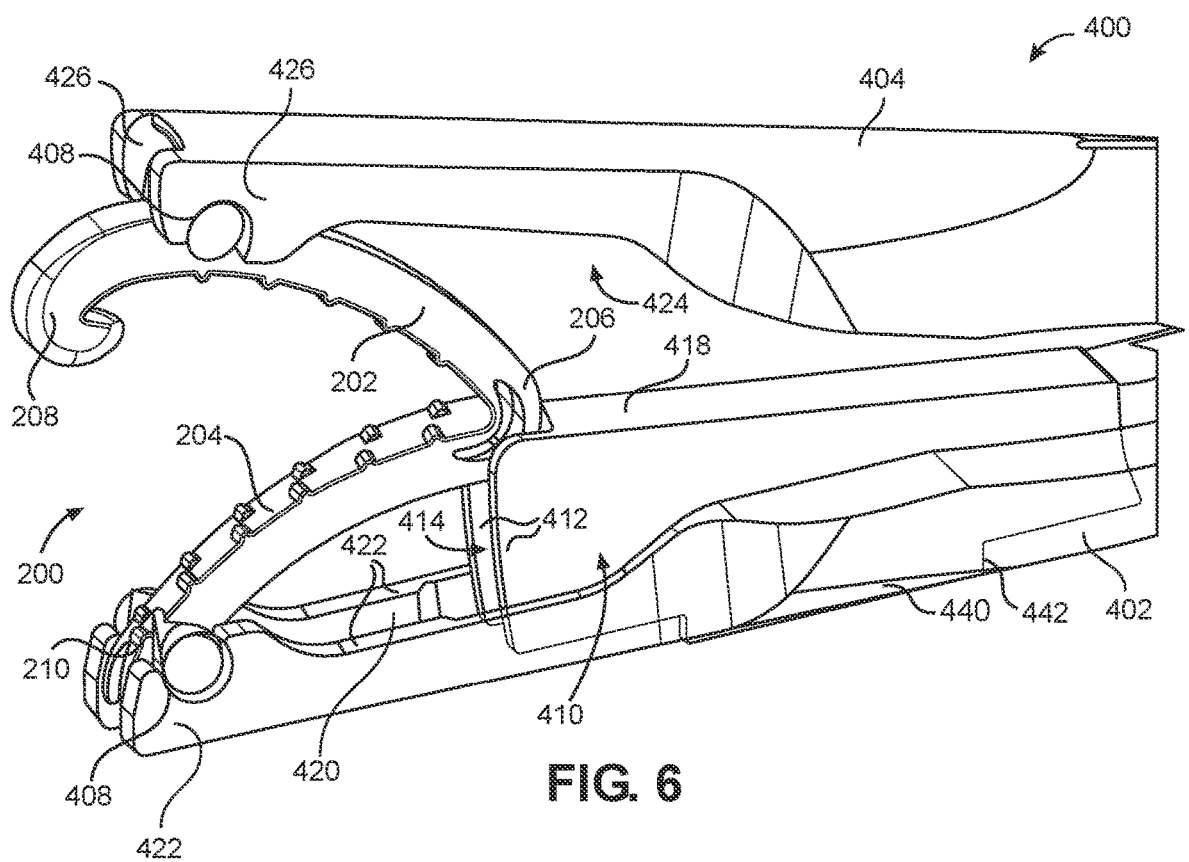
FIG. 6 illustrates a perspective view of a third exemplary embodiment of a clip applier having an exemplary stabilizing member of the present disclosure.

FIG. 6 illustrates a clip applier 400 loaded with the surgical clip 200 in an open configuration. As illustrated, the clip applier 400 may have a first jaw member 402 and a second jaw member 404 pivotably coupled at a hinge member (not shown). The first and second jaw members 402, 404 may be configured to compress the surgical clip 200, as similar discussed above.

As further illustrated, the first and second jaw members 402, 404 may include at least one recess 408 at a distal portion and a stabilizing member 410 proximal of the at least one recess 408. The at least one recess 408 may extend transversely through the first and second jaw members 402, 404 and be configured to receive a boss member 212 on the first and second leg members 202, 204 of the surgical clip 200 in an interference or snap-fit. A first longitudinal channel 420 may extend through an inner portion of the first jaw member 402, separating the first jaw member 402 into a pair of first extensions 422. A second longitudinal channel 424 may extend through an inner portion of the second jaw member 404, separating the second jaw member 404 into a pair of second extensions 426. Each of the extensions 422, 426 may have a recess 408 configured to receive opposing boss members 212, and each of the first and second longitudinal channels 420, 424 may be configured to receive a portion of the surgical clip 200. The first longitudinal channel 420 may be configured to receive a first end portion of the stabilizing member 410 (as illustrated in FIG. 6), the second longitudinal channel 424 may include a wider proximal portion (not shown) configured to receive a second end portion of the stabilizing member 410 when the first and second jaw members 402, 404 are in a closed configuration (as similarly illustrated in FIGS. 3A-B).

The stabilizing member 410 may be configured to align the surgical clip 200 by reducing lateral movement of a proximal portion. The stabilizing member 410 may be removably secured to the first jaw member 402 and extend inwardly from the first jaw member 402 toward the second jaw member 404. The stabilizing member 410 may have first and second longitudinal walls 412 having substantially inner and/or outer side surfaces that do not hinder closure of the clip applier 400 and/or the surgical clip 200. The longitudinal walls 412 may define a cavity 414 therebetween, and the longitudinal walls 412 may be joined to close the cavity 514 at the proximal end. The stabilizing member 410 may not proximally abut the proximal portion of the surgical clip 200 when the first and second jaw members 402, 404 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 410 may have an inner portion 418 (e.g., the corners of the longitudinal walls 412) that overlaps the surgical clip 200 when the first and second jaw members 402, 404 are in an open configuration. Therefore, in the open configuration, the stabilizing member 410 may receive the surgical clip in the cavity 414, and the first and second longitudinal walls 412 may overlap the proximal portion of the surgical clip 200. As the first and second jaw members 402, 404 close, the stabilizing member 410 may slide over the proximal portion of the surgical clip 200, and the second longitudinal channel 424 may receive the stabilizing member 410 while the surgical clip 200 is received in the cavity 414.

Figure 7:
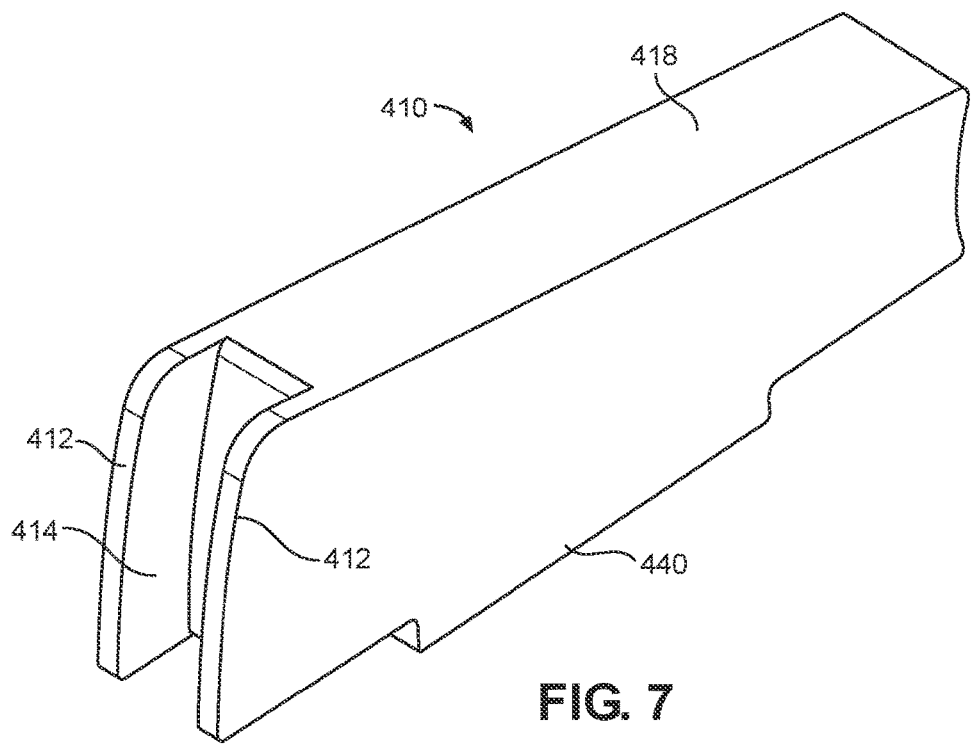
FIG. 7 illustrates a perspective view of the exemplary stabilizing member of the third exemplary embodiment of FIG. 6.

As further illustrated in FIG. 7, the stabilizing member 410 may include a block having a length configured to extend along the inner surface of the jaw members 402, 404, substantially larger than a height and width. The inner portion 418 of the stabilizing member 410 may have a tapered inner flat surface that abuts a substantially flat inner wall (not shown) of the second longitudinal channel 424 in the closed configuration to provide a stop. As illustrated in FIG. 6, the stabilizing member 410 may be secured in the longitudinal channel 420 of the first jaw member 402, and further include a securing member (e.g., a projection) 440 configured to releasably engage and/or interlock a securing member (e.g., a slot) 442 in the first jaw member 402. An interference and/or snap fit may be created between the projection 440 and the slot 442 to releasably secure the stabilizing member 410 to the first jaw member 402. The stabilizing member 410 may therefore be a single-use component that may be removed and/or disposed of, for example, after a surgical procedure. In that sense, the stabilizing member 410 may be used to apply one or more surgical clips 200 to ligate tissue, and the stabilizing member 410 may then be removed from the clip applier 400 and disposed of. The stabilizing member 410 may therefore be composed of an inexpensive plastic that may be readily replaced if damaged.

Figure 8:
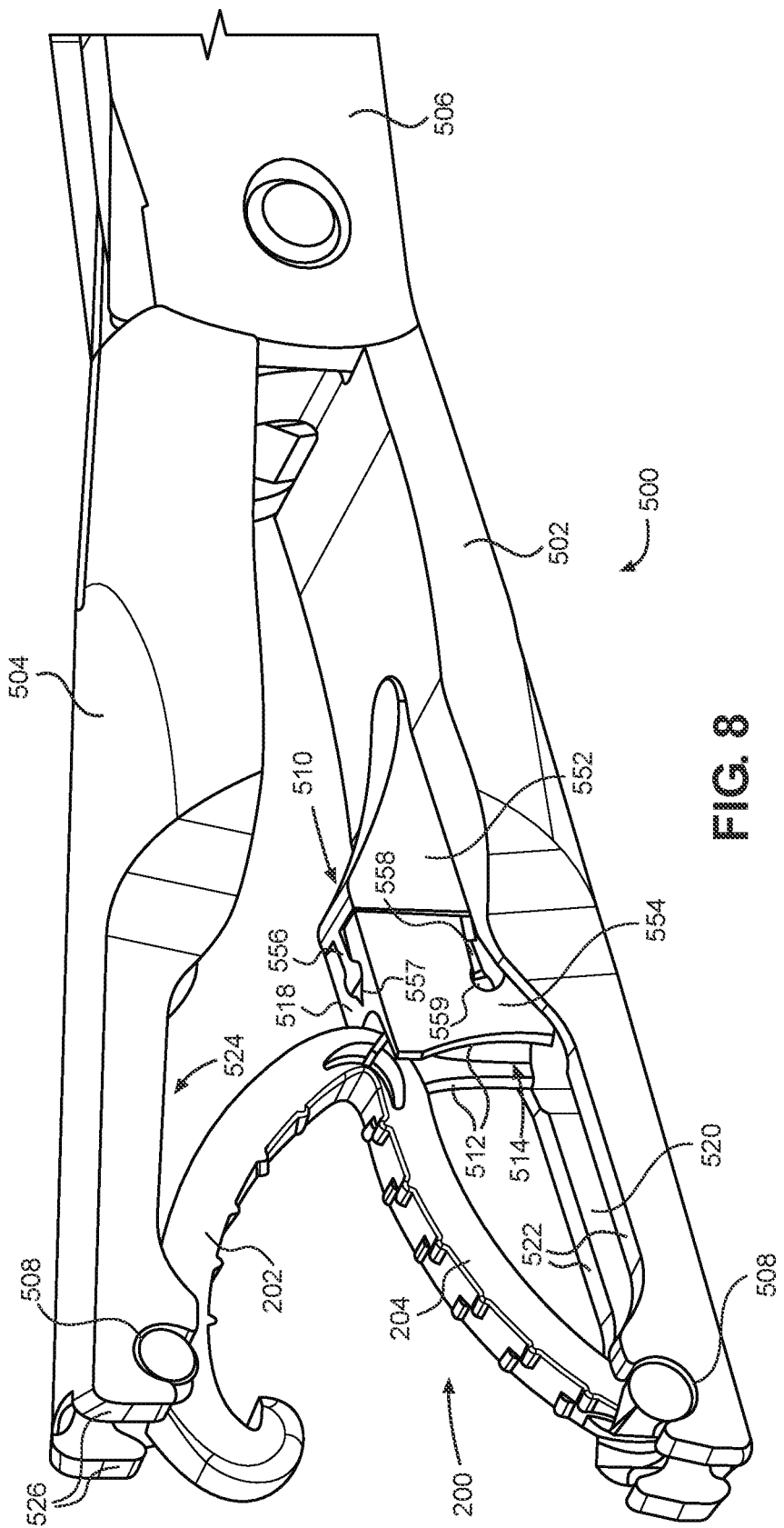
FIG. 8 illustrates a perspective view a fourth exemplary embodiment of a clip applier having an exemplary stabilizing member and loaded with an exemplary surgical clip of the present disclosure.

FIG. 8 illustrates a clip applier 500 loaded with the surgical clip 200 in an open configuration. As illustrated, the clip applier 500 may have a first jaw member 502 and a second jaw member 504 pivotably coupled at a hinge member 506. The first and second jaw members 502, 504 may be configured to compress the surgical clip 200, as similar discussed above.

As further illustrated, the first and second jaw members 502, 504 may include at least one recess 508 at a distal portion and a stabilizing member 510 proximal of the at least one recess 508. The at least one recess 508 may extend transversely through the first and second jaw members 502, 504 and be configured to receive a boss member 212 on the first and second leg members 202, 204 of the surgical clip 200 in an interference or snap-fit. A first longitudinal channel 520 may extend through an inner portion of the first jaw member 502, separating the first jaw member 502 into a pair of first extensions 522. A second longitudinal channel 524 may extend through an inner portion of the second jaw member 504, separating the second jaw member 504 into a pair of second extensions 526. Each of the extensions 522, 526 may have a recess 508 configured to receive opposing boss members 212, and each of the first and second longitudinal channels 520, 524 may be configured to receive a portion of the surgical clip 200. The first longitudinal channel 520 may be configured to receive a first end portion of the stabilizing member 510 (as illustrated in FIG. 8), the second longitudinal channel 524 may include a wider proximal portion (not shown) configured to receive a second end portion of the stabilizing member 510 when the first and second jaw members 502, 504 are in a closed configuration (as similarly illustrated in FIGS. 3A-B).

The stabilizing member 510 may be configured to align the surgical clip 200 by reducing lateral movement of a proximal portion. The stabilizing member 510 may have a first proximal portion 552 integrally fixed to the first jaw member 502 and a second distal portion 554 removably secured to the first portion 552. The second portion 554 may have first and second longitudinal walls 512 having substantially flat inner and/or outer side surfaces that do not hinder closure of the clip applier 500 and/or the surgical clip 200. The longitudinal walls 512 may define a cavity 514 therebetween, and the longitudinal walls 512 may be joined to close the cavity 514 at the proximal end. The stabilizing member 510 may not proximally abut the proximal portion of the surgical clip 200 when the first and second jaw members 502, 504 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 510 may have an inner portion 518 (e.g., the corners of the longitudinal walls 412) that overlaps the surgical clip 200 when the first and second jaw members 502, 504 are in an open configuration. Therefore, in the open configuration, the stabilizing member 510 may receive the surgical clip in the cavity 514, and the first and second longitudinal walls 512 may overlap the proximal portion of the surgical clip 200. As the first and second jaw members 502, 504 close, the stabilizing member 510 may slide over the proximal portion of the surgical clip 200, and the second longitudinal channel 524 may receive the stabilizing member 510 while the surgical clip 200 is received in the cavity 514.

As further illustrated in FIG. 8, the second portion 554 may be a block releasably secured to the first portion 552. The second portion 554 may be releasably secured to the first portion 552 through a number of different manners. For example, as illustrated in FIG. 8, the first portion 552 may have first and second male members 556, 558, each having enlarged distal ends. The first male member 556 may extend vertically through a vertical slot 557 of the second member 554, and the second male member 558 may extend laterally through a lateral slot 559 of the second member 554. In this manner, the interaction between the male members 556, 228 and the slots 557, 559 may secure the second portion 554 onto the first jaw member 502 in vertical and lateral directions. The enlarged distal ends may allow the second portion 554 to snap onto the first portion 552 in an interference fit to facilitate attachment and removal. In another embodiment, the first portion 552 may have a plurality of prongs configured to be received in apertures on the second portion 554 to secure the second portion 554 to the first jaw member 502. The stabilizing member 510 may be a single-use component that may be removed and/or disposed of, for example, after a surgical procedure. In that sense, the stabilizing member 510 may be used to apply one or more surgical clips 200 to ligate tissue, and the stabilizing member 510 may then be removed from the clip applier 500 and disposed of. The stabilizing member 410 may therefore be composed of an inexpensive plastic that may be readily replaced if damaged.

Figure 9:
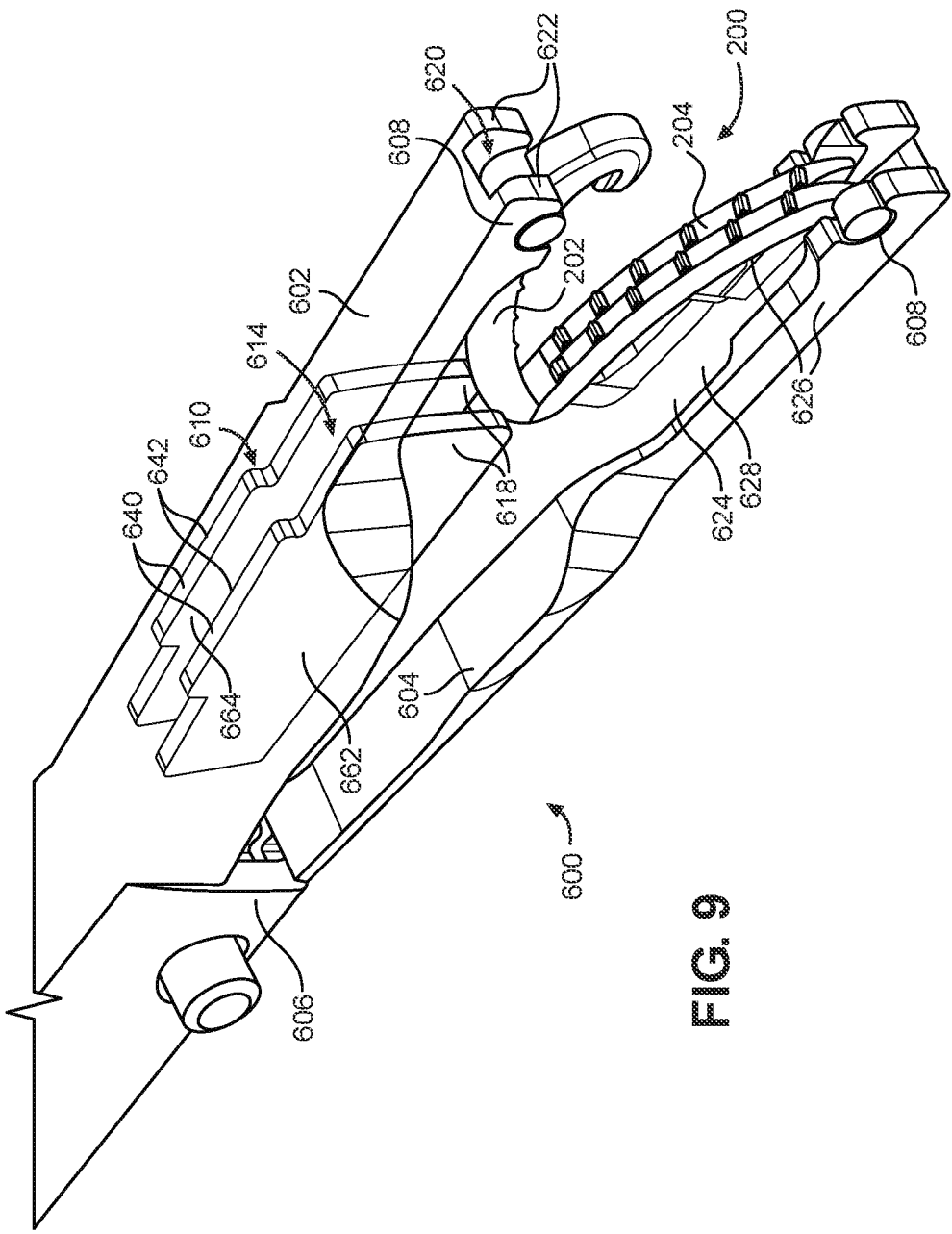
FIG. 9 illustrates a perspective view a fifth exemplary embodiment of a clip applier having an exemplary stabilizing member and loaded with an exemplary surgical clip of the present disclosure.

FIG. 9 illustrates a clip applier 600 loaded with the surgical clip 200 in an open configuration. As illustrated, the clip applier 600 may have a first jaw member 602 and a second jaw member 604 pivotably coupled at a hinge member 606. The first and second jaw members 602, 604 may be configured to compress the surgical clip 200, as similar discussed above.

As further illustrated, the first and second jaw members 602, 604 may include at least one recess 608 at a distal portion and a stabilizing member 610 proximal of the at least one recess 608. The at least one recess 608 may extend transversely through the first and second jaw members 602, 604 and be configured to receive a boss member 212 on the first and second leg members 202, 204 of the surgical clip 200 in an interference or snap-fit. A first longitudinal channel 620 may extend through an inner portion of the first jaw member 602, separating the first jaw member 602 into a pair of first extensions 622. A second longitudinal channel 624 may extend through an inner portion of the second jaw member 604, separating the second jaw member 604 into a pair of second extensions 626. Each of the extensions 622, 626 may have a recess 608 configured to receive opposing boss members 212, and each of the first and second longitudinal channels 620, 624 may be configured to receive a portion of the surgical clip 200. The first longitudinal channel 620 may be configured to receive a first end portion of the stabilizing member 610 in an open configuration (as illustrated in FIG. 9), the second longitudinal channel 624 may include a wider proximal portion 628 configured to receive a second end portion of the stabilizing member 610 when the first and second jaw members 602, 604 are in a closed configuration (as similarly illustrated in FIGS. 3A-B).

The stabilizing member 610 may include first and second longitudinal plates or walls 662, 664 separated laterally and configured to align the surgical clip 200 by reducing lateral movement of a proximal portion. The longitudinal walls 662, 664 may extend inwardly from the first jaw member 602. The longitudinal walls 662, 664 may be removably secured to the first jaw member 602 and extend inwardly toward the second jaw member 604. The longitudinal walls 662, 664 having substantially flat inner and/or outer side surfaces that do not hinder closure of the clip applier 600 and/or the surgical clip 200. The longitudinal walls 662, 664 may define a cavity 614 therebetween and may extend parallel, having spaced apart proximal and distal ends. The stabilizing member 610 may not proximally abut the proximal portion of the surgical clip 200 when the first and second jaw members 602, 604 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 610 may have an inner portion 618 (e.g., the corners of the longitudinal walls 662, 664) that overlaps the surgical clip 200 when the first and second jaw members 602, 604 are in an open configuration. Therefore, in the open configuration, the stabilizing member 610 may receive the surgical clip in the cavity 614, and the first and second longitudinal walls 662, 664 may overlap the proximal portion of the surgical clip 200. As the first and second jaw members 602, 604 close, the stabilizing member 610 may slide over the proximal portion of the surgical clip 200, and the second longitudinal channel 624 may receive the stabilizing member 610 while the surgical clip 200 is received in the cavity 614.

As further illustrated, the first and second longitudinal plates or walls 662, 664 may be separate components, each releasably attached to the first jaw member 602. The first and second longitudinal walls 662, 664 may be secured in the longitudinal channel 620 of the first jaw member 602, and each include a securing member (e.g., a projection) 640 configured to releasably engage and/or interlock a securing member (e.g., a slot) 642 in the first jaw member 602. An interference and/or snap fit may be created between the projection 640 and the slot 642 to releasably secure the stabilizing member 610 to the first jaw member 602. The stabilizing member 610 may therefore include single-use components that may be removed and/or disposed of, for example, after a surgical procedure. In that sense, the stabilizing member 610 may be used to apply one or more surgical clips 200 to ligate tissue, and the stabilizing member 610 may then be removed from the clip applier 600 and disposed of. The stabilizing member 410 may therefore be composed of an inexpensive plastic that may be readily replaced if damaged.

Figure 10:
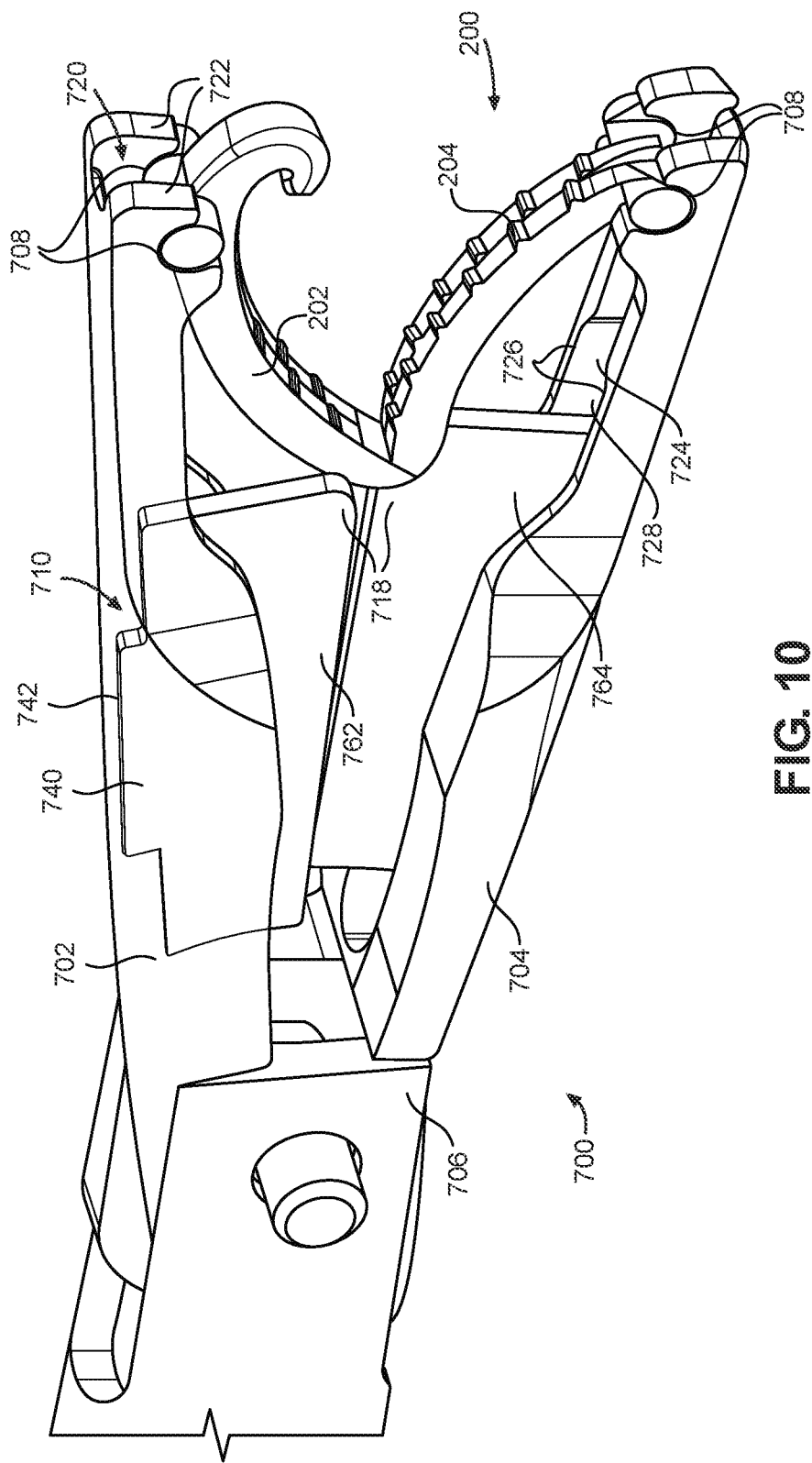
FIG. 10 illustrates a perspective view a sixth exemplary embodiment of a clip applier having an exemplary stabilizing member and loaded with an exemplary surgical clip of the present disclosure.

FIG. 10 illustrates a clip applier 700 loaded with the surgical clip 200 in an open configuration. As illustrated, the clip applier 700 may have a first jaw member 702 and a second jaw member 704 pivotably coupled at a hinge member 706. The first and second jaw members 702, 704 may be configured to compress the surgical clip 200, as similar discussed above.

As further illustrated, the first and second jaw members 702, 704 may include at least one recess 708 at a distal portion and a stabilizing member 710 proximal of the at least one recess 708. The at least one recess 708 may extend transversely through the first and second jaw members 702, 704 and be configured to receive a boss member 212 on the first and second leg members 202, 204 of the surgical clip 200 in an interference or snap-fit. A first longitudinal channel 720 may extend through an inner portion of the first jaw member 702, separating the first jaw member 702 into a pair of first extensions 722. A second longitudinal channel 724 may extend through an inner portion of the second jaw member 704, separating the second jaw member 704 into a pair of second extensions 726. Each of the extensions 722, 726 may have a recess 708 configured to receive opposing boss members 212, and each of the first and second longitudinal channels 720, 724 may be configured to receive a portion of the surgical clip 200. In an open configuration, each of the first and second longitudinal channel 720, 724 may have a wider proximal portion 628 that receives a first end portion of one of the longitudinal walls 762, 764, as illustrated in FIG. 10. In a closed configuration, the wider proximal portion 728 of the opposing first and second longitudinal channel 720, 724 may receive a second end portion of the other longitudinal wall 762, 764. Therefore, each of the wider proximal portions 728 may be configured to receive both longitudinal walls 762, 764 in the closed configuration.

The stabilizing member 710 may be configured to align the surgical clip 200 by reducing lateral movement of a proximal portion. The stabilizing member 710 may include a first longitudinal plate or wall 762 extending inwardly from the first jaw member 702 and a second longitudinal plate or wall 764 extending inwardly from the second jaw member 704 The longitudinal walls 762, 764 may be removably secured to the respective jaw member 702, 704 and have substantially flat inner and/or outer side surfaces that do not hinder closure of the clip applier 700 and/or the surgical clip 200. The longitudinal walls 712 may define a space therebetween and may have spaced apart proximal and distal ends. The stabilizing member 710 may not proximally abut the proximal portion of the surgical clip 200 when the first and second jaw members 702, 704 are in an open configuration and throughout closure, by providing a space proximal of the proximal portion of the surgical clip 200. The proximal space may allow the curved leg members 202, 204 to pivot, straighten, and/or lengthen as the surgical clip 200 closes and the hook member 208 deflects around the tip member 210. The stabilizing member 710 may have an inner portion 718 (e.g., the corners of the longitudinal walls 762, 764) that overlaps the surgical clip 200 when the first and second jaw members 702, 704 are in an open configuration. Therefore, in the open configuration, the stabilizing member 710 may receive the surgical clip in the space, and the first and second longitudinal walls 762, 764 may overlap the proximal portion of the surgical clip 200. As the first and second jaw members 702, 704 close, the stabilizing member 610 may slide over the proximal portion of the surgical clip 200, and the second longitudinal channel 724 may receive the stabilizing member 710 while the surgical clip 200 is received in the space.

As further illustrated, the first and second longitudinal plates or walls 762, 764 may be separate components, each releasably attached to the respective jaw member 702, 704. The first and second longitudinal walls 762, 764 may be secured in the longitudinal channels 720, 724 of the respective jaw member 702, 704, and each include a securing member (e.g., a projection) 740 configured to releasably engage and/or interlock a securing member (e.g., a slot) 742 in the jaw member 702, 704. An interference and/or snap fit may be created between the projection 740 and the slot 742 to releasably secure the longitudinal walls 762, 764 to the jaw members 702, 704. The stabilizing member 710 may therefore include single-use components that may be removed and/or disposed of, for example, after a surgical procedure. In that sense, the stabilizing member 710 may be used to apply one or more surgical clips 200 to ligate tissue, and the stabilizing member 710 may then be removed from the clip applier 700 and disposed of. The stabilizing member 410 may therefore be composed of an inexpensive plastic that may be readily replaced if damaged.

The various embodiments of the clip applier may therefore provide at least three-points of contact with the surgical clip. The clip applier may engage the distal portion of the surgical clip with the engagement of the recesses to the boss members, and the clip applier may laterally align the surgical clip by receiving the proximal portion of the surgical clip in the cavity of the stabilizing member. The longitudinal walls may reduce lateral movement of the proximal portion and prevent the surgical clip from fish-tailing.

The various embodiments of the surgical clip of the present disclosure may be made of any suitable size and may be applied to any number of tissues, such as blood vessels, lymph nodes, nerves, fallopian tubes, or cardiac tissue. The surgical clip may be constructed from any suitable biocompatible material, such as certain metals and polymers. However, the present invention is particularly suitable for practice with polymeric clips. Thus, the surgical clip preferably has a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip to tissue, the clip applier comprising:
    a first jaw member configured to engage a distal portion of a first leg member of the surgical clip;
    a second jaw member configured to engage a distal portion of a second leg member of the surgical clip;
    a first stabilizing member extending from the first jaw member;
    a second stabilizing member extending from the second jaw member, wherein the first and second stabilizing members define a space therebetween configured to receive a proximal portion of the surgical clip and to reduce lateral movement of the surgical clip;
    a first channel on an inner surface of the first jaw member configured to receive the second stabilizing member when the first and second jaw members are in a closed configuration; and
    a second channel on an inner surface of the second jaw member configured to receive the first stabilizing member when the first and second jaw members are in the closed configuration.

2. The clip applier of claim 1, wherein the first and second stabilizing members do not proximally abut the surgical clip when the first and second jaw members are in an open configuration.

3. The clip applier of claim 1, wherein the first stabilizing member comprises a first longitudinal wall, the second stabilizing member comprises a second longitudinal wall, and the second longitudinal walls are configured to receive the proximal portion of the surgical clip when the first and second jaw members are in an open configuration.

4. The clip applier of claim 3, wherein the first and second longitudinal walls have substantially flat inner side surfaces.

5. The clip applier of claim 3, wherein a proximal end of the space is open.

6. The clip applier of claim 1, wherein the first and second stabilizing members are configured to slide over the proximal portion of the surgical clip when the clip applier closes.

7. The clip applier of claim 1, further comprising:
    at least one first recess on the distal portion of the first jaw member, the at least one first recess configured to receive a first boss member of the surgical clip on the distal portion of the first leg member; and
    at least one second recess on the distal portion of the second jaw member, the at least one second recess configured to receive a second boss member of the surgical clip on the distal portion of the second leg member.

8. The clip applier of claim 1, wherein the first stabilizing member is removably secured to the first jaw member, and the second stabilizing member is removably secured to the second jaw member.

9. The clip applier of claim 1, wherein the first channel extends longitudinally along the first jaw member and is configured to receive a portion of the first leg member, and the second channel extends longitudinally along the second jaw member and is configured to receive a portion of the second leg member.

10. The clip applier of claim 1, wherein the first stabilizing member is integrally fixed to the first jaw member, and the second stabilizing member is integrally fixed to the second jaw member.

11. A method of loading a clip applier with a surgical clip, the surgical clip comprising first and second leg members, the method comprising:
    engaging a distal portion of the first leg member with a first jaw member of the clip applier;
    engaging a distal portion of the second leg member with a second jaw member of the clip applier; and
    receiving a proximal portion of the surgical clip between a first stabilizing member extending from the first jaw member and a second stabilizing member extending from the second jaw member to reduce lateral movement of the surgical clip;
    pivoting at least one of the first and second jaw members into a closed configuration;
    receiving the first stabilizing member in a second channel on an inner surface of the second jaw member in the closed configuration; and
    receiving the second stabilizing member in a first channel on an inner surface of the first jaw member in the closed configuration.

12. The method of claim 11, wherein receiving the proximal portion of the surgical clip comprises receiving the proximal portion between a first longitudinal wall of the first jaw member and a second longitudinal wall of the second jaw member.

13. The method of claim 11, wherein receiving the proximal portion of the surgical clip provides a space proximal of the proximal portion when the first and second jaw members are in an open configuration to allow at least one of the first and second leg members to lengthen during closure of the surgical clip.

14. The method of claim 11, further comprising:
    pivoting the first and second jaw members into a closed configuration;
    sliding the first stabilizing member over the proximal portion of the surgical clip; and
    sliding the second stabilizing member over the proximal portion of the surgical clip.

15. The method of claim 11,
    wherein engaging the distal portion of the first leg member comprises receiving a first boss member into at least one first recess on a distal portion of the first jaw member, and
    wherein engaging the distal portion of the second leg member comprises receiving a second boss member into at least one second recess on a distal portion of the second jaw member.

16. The method of claim 11, further comprising receiving a portion of the first leg member in the first channel, and receiving a portion of the second leg member in the second channel.

17. The method of claim 11, further comprising removing the first and second stabilizing members from the clip applier.

18. An assembly comprising:
    a surgical clip comprising a first leg member having a first boss member at a distal portion and a second leg member having a second boss member at a distal portion;

a clip applier comprising:
- a first jaw member comprising a first recess on a distal portion receiving the first boss member;
- a second jaw member comprising a second recess on a distal portion receiving the second boss member;
- a first stabilizing member extending from an inner surface of the first jaw member; and
- a second stabilizing member extending from an inner surface of the second jaw member, wherein the first and second stabilizing members define a space therebetween configured to receive a proximal portion of the surgical clip and to reduce lateral movement of the surgical clip;
- a first channel on an inner surface of the first jaw member configured to receive the second stabilizing member when the first and second jaw members are in a closed configuration; and
- a second channel on an inner surface of the second jaw member configured to receive the first stabilizing member when the first and second jaw members are in the closed configuration.

19. The assembly of claim 18, wherein the clip applier does not proximally abut the proximal portion of the surgical clip when the first and second jaw members are in an open configuration.

20. The assembly of claim 18, wherein the proximal portion of the surgical clip includes a hinge portion.

* * * * *